US008652097B2

(12) United States Patent
Lee

(10) Patent No.: US 8,652,097 B2
(45) Date of Patent: Feb. 18, 2014

(54) SYSTEMS AND METHODS FOR COMBINING MATERIALS

(75) Inventor: Freddie Eng Hwee Lee, Singapore (SG)

(73) Assignee: B. Braun Melsungen AG, Melsungen (DE)

( * ) Notice: Subject to any disclaimer, the term of this patent is extended or adjusted under 35 U.S.C. 154(b) by 253 days.

(21) Appl. No.: 13/230,996

(22) Filed: Sep. 13, 2011

(65) Prior Publication Data

US 2012/0035537 A1 Feb. 9, 2012

Related U.S. Application Data

(62) Division of application No. 12/062,702, filed on Apr. 4, 2008, now Pat. No. 8,034,044.

(51) Int. Cl.
*A61M 37/00* (2006.01)

(52) U.S. Cl.
USPC .......... 604/83

(58) Field of Classification Search
USPC .......... 604/83–92, 500, 506, 507, 518
See application file for complete search history.

(56) References Cited

U.S. PATENT DOCUMENTS

| | | | |
|---|---|---|---|
| 4,243,080 A | 1/1981 | Choksi | |
| 5,105,983 A | 4/1992 | Sancoff et al. | |
| 6,645,181 B1 | 11/2003 | Lavi | |
| 7,618,432 B2 | 11/2009 | Pedersen et al. | |

FOREIGN PATENT DOCUMENTS

| | | |
|---|---|---|
| EP | 0327519 | 8/1989 |
| WO | 9311709 | 6/1993 |
| WO | 2007122209 | 11/2007 |
| WO | WO 2007/122209 A1 * | 11/2007 |
| WO | 2007147741 | 12/2007 |

OTHER PUBLICATIONS

Office Action for U.S. Appl. No. 12/835,209 mailed Feb. 2, 2012.

* cited by examiner

*Primary Examiner* — Nicholas Lucchesi
*Assistant Examiner* — Pritesh Patel
(74) *Attorney, Agent, or Firm* — RatnerPrestia

(57) ABSTRACT

A method of combining a drug in a first container and a liquid in a second container includes placing the first container and the second container in fluid communication with a housing, combining the liquid and the drug in the first container, transferring the liquid and the drug from the first container to the housing, and transferring the liquid and the drug from the housing to a third container.

13 Claims, 3 Drawing Sheets

FIG 6 A
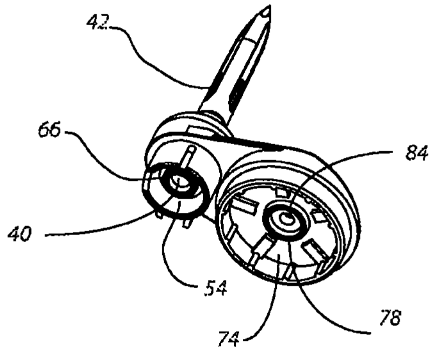
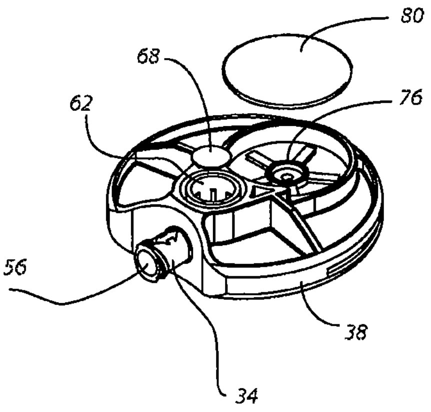
FIG 6 B
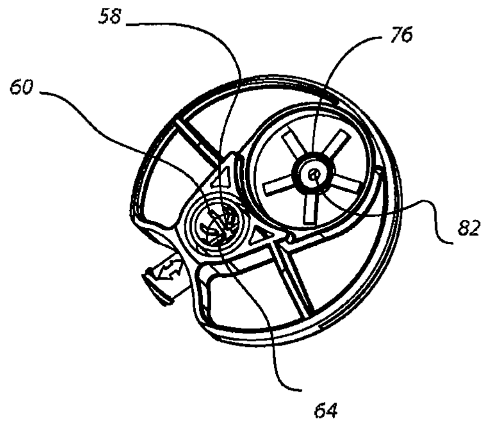
FIG 6 C

SYSTEMS AND METHODS FOR COMBINING MATERIALS

CROSS REFERENCE TO RELATED APPLICATIONS

This patent application is a divisional of U.S. application Ser. No. 12/062,702, filed Apr. 4, 2008 the contents of which are incorporated herein by reference.

FIELD OF THE INVENTION

The invention relates to devices, systems and methods for combining materials, for example, a drug with another material, such as a liquid.

BACKGROUND

In the medical field, preparations of certain drugs (such as an intravenous or IV drug) can involve reconstituting and/or diluting a drug (e.g., in the form of a dry powder or a liquid in a drug vial) with an appropriate solution/diluent. The solution/diluent can be delivered from a first vessel to a second vessel containing the drug using a needle and a syringe. Sometimes, further dilution is performed, which is done by injecting the reconstituted/diluted drug into an infusion bag via an injection port of the bag. More recent infusion bag designs, either empty or pre-filled, allow the dilution to take place with transfer spikes that fluidly connects the bag and the vessel containing the drug.

SUMMARY

The invention relates to devices, systems and methods for combining materials, for example, a drug with another material, such as a liquid diluent. In some embodiments, the devices, systems and methods allow a drug to be combined with a liquid to a selected concentration (e.g., for reconstitution and/or mixing of the drug), and the resulting combination to be transferred to a reservoir (such as a bag or a pump) for subsequent administration to a patient. The combination and transfer can be performed in a manner that does not substantially expose the drug or the user to potential contaminants.

In one aspect, the invention features a method including a method of combining a drug in a first container and a liquid in a second container, the method including placing the first container and the second container in fluid communication with a housing; combining the liquid and the drug in the first container; transferring the liquid and the drug from the first container to the housing; and transferring the liquid and the drug from the housing to a third container.

Embodiments may include one or more of the following features. The method further includes restricting flow of the liquid from the housing to the first container. The method further includes restricting air flow into the housing. The method further includes allowing air flow out of the housing. The method further includes restricting air flow into the housing, and allowing air flow out of the housing. The method further includes restricting air flow into the third container. Transferring the liquid and the drug from the first container to the housing; and transferring the liquid and the drug from the housing to a third container are facilitated by a pump associated with the housing. The method further includes restricting flow of the liquid from the third container to the housing. Transferring the liquid and the drug from the housing to the third container includes flowing the liquid and the drug at a pressure greater than one atmosphere. The method further includes displacing air from the first container and the housing. Transferring the liquid and the drug to the housing or to the third container includes activating at least two one-way flow valves. The housing contains an air filter, and the method further includes preventing the liquid from contacting the air filter.

In another aspect, the invention features a system including a medical device system, including a medical device having a housing configured to be placed in fluid communication with a first container containing a drug, a second container containing a liquid, a pump, and a third container, wherein the medical device is configured to combine the liquid and the drug in the first container, to transfer the liquid and the drug from the first container to the housing, and to transfer the liquid and the drug from the housing to the third container.

Embodiments may include one or more of the following features. The medical device includes a one-way flow valve adapted to restrict flow of the liquid from the housing to the first container. The medical device includes a valve adapted to restrict air flow into the housing. The medical device includes a valve adapted to restrict air flow into the housing and to allow air flow out of the housing. The valve includes a movable member responsive to a level of liquid in a chamber containing the movable member. The medical device includes a valve adapted to restrict liquid flow into the third container. The medical device includes a one-way flow valve adapted to restrict liquid flow from the third container to the housing. The medical device includes at least two one-way flow valves in the housing. The medical device includes at least three flow valves in the housing. The medical device includes at least two piercing elements in fluid communication with the housing. The medical device includes an air filter, and the medical device is configured to restrict the air filter from contacting the liquid. The system further includes the first container, the second container, the pump in the form of a syringe, and a third container.

Embodiments may further include one or more of the following advantages.

The devices, systems and methods can be easily used and performed, with almost no or minimal training, and in an integrated and seamless fashion. For example, no priming of conduits carrying fluids is required as encapsulated air can be displaced or purged during use. No valves or air vent caps need to be manipulated to perform the combination and transfer of materials.

Combination and transfer of one or more selected materials can occur in a closed system. Air trapped in a drug container can be purged from the closed system, while air is prevented from entering into the system (e.g., into a container from which the drug is administered to the patient). Combining and transferring the material(s) in a closed system can reduce the risks of injuries from exposed needles, microbiological or particulate contamination resulting from poor aseptic techniques, aerosolized drugs, and/or exposure of personnel to the drugs and the contaminants. Piercing elements (such as spikes and needles) need not be removed and re-engaged during use, which enhances safety to the medical personnel and patient, and reduces possible contamination of the materials to be administered.

The combination and transfer can also be efficiently applied to drug preparations having relatively high viscosities.

The details of one or more embodiments are set forth in the accompanying description below. Other aspects, features, and advantages of the invention will be apparent from the following drawings, detailed description of embodiments, and also from the appending claims.

BRIEF DESCRIPTION OF DRAWINGS

FIG. 6A is a perspective view of a portion of the medical device shown in FIG. 2; FIG. 6B is another perspective view of a portion of the medical device shown in FIG. 2; and FIG. 6C is another perspective view of a portion of the medical device shown in FIG. 2;

DETAILED DESCRIPTION

Figure 1:
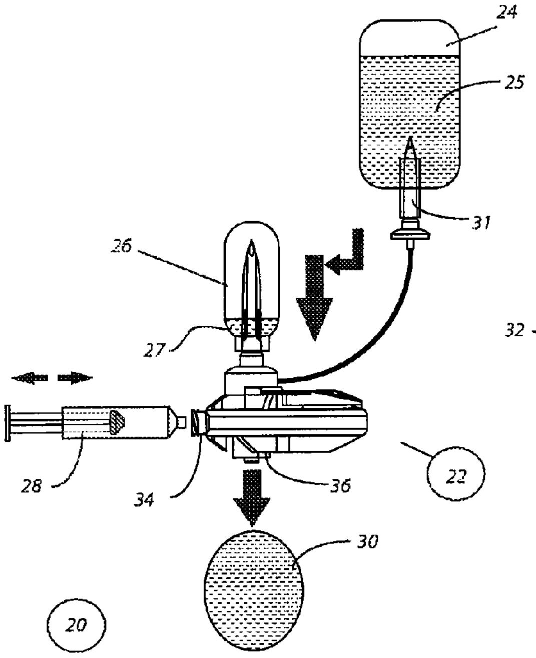
FIG. 1 is a schematic diagram of an embodiment of a medical device system.

FIG. 1 shows a medical device system 20 including a medical device 22 that is in fluid (e.g. liquid) communication with a reservoir 24 containing a liquid 25, a container (as shown, a vial 26) containing a drug 27, a pump (as shown, a syringe 28), and a target container 30 (such as a bag or a bottle). Medical device 22 is capable of being used to transfer liquid 25 from reservoir 24 into vial 26 and the medical device, to combine drug 27 and the liquid, and to transfer the drug and liquid combination into target container 30. As described herein, the combining and transferring of liquid 25 and drug 27 can be performed without exposing the drug and liquid combination to any air or excessive air or microbiological contamination, without introducing any air or excessive air into target container 30, and without exposing a user (e.g., medical personnel) to aerosolized materials.

Figure 2:
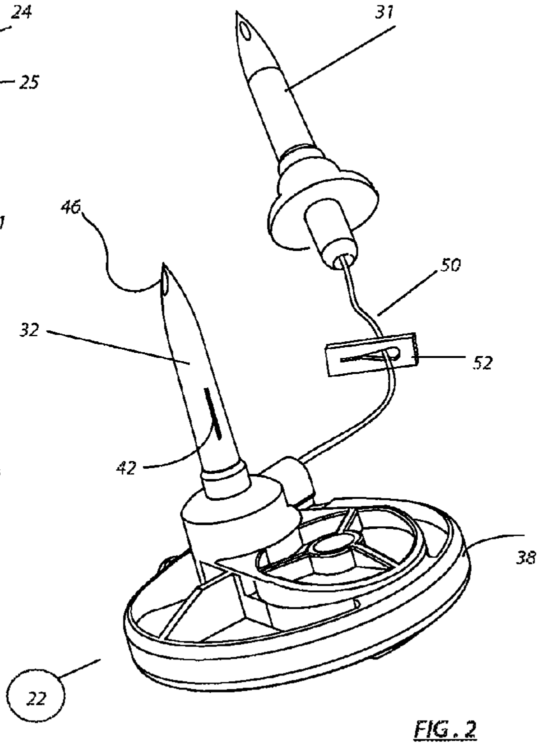
FIG. 2 is a perspective view of an embodiment of a medical device.
Figure 3:
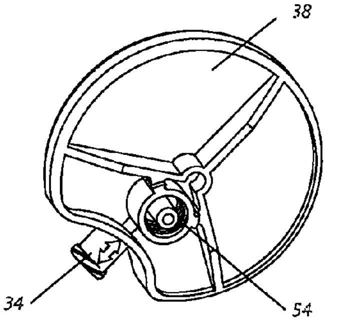
FIG. 3 is a partial, perspective view of an embodiment of a housing.
Figure 4A:
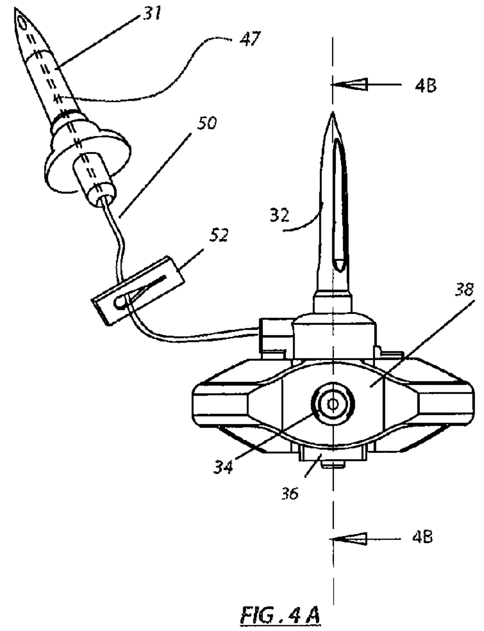
FIG. 4A is a side view of the medical device shown in FIG. 2.
Figure 4B:
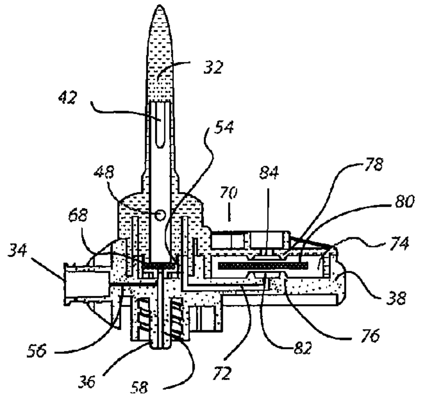
FIG. 4B is a cross-sectional view of the medical device shown in FIG. 4A, taken along line 4B-4B.

Referring also to FIGS. 2 and 3, medical device 22 is capable of being in fluid communication with reservoir 24, vial 26, syringe 28, and target container 30 through multiple piercing members and ports. More specifically, medical device 22 includes a transfer spike 31 and a vial spike 32 that can be used to place the medical device in fluid communication with reservoir 25 and vial 26, respectively. Spikes 31, 32, each of which includes an internal passageway, are configured to engage with reservoir 24 and vial 26 (e.g., by piercing through a septum or a seal) and to place liquid 25 and drug 27 in fluid communication with medical device 22. Medical device 22 further includes an activation port 34 configured to engage with syringe 28, and an outlet port 36 configured to engage with target container 30. As shown, ports 34, 36 includes Luer-type connections to facilitate engagement and disengagement with syringe 28 and target container 30, but other connections (temporary (e.g., quick-connect) or permanent) can be used.

Figure 5A:
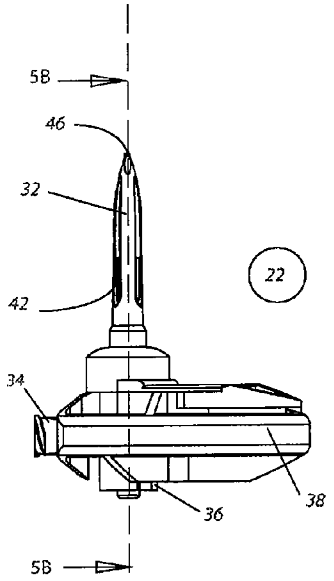
FIG. 5A is a partial, side view of the medical device shown in FIG. 2.
Figure 5B:
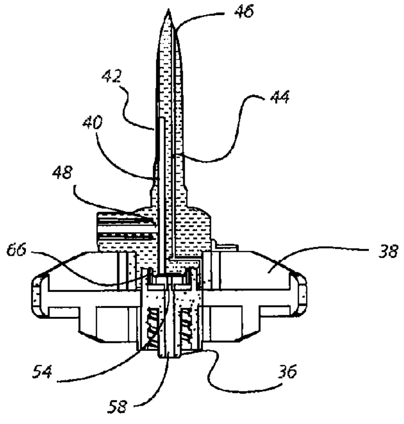
FIG. 5B is a cross-sectional view of the medical device shown in FIG. 5A, taken along line 5B-5B.

Referring to FIGS. 4A, 4B, 5A, and 5B, medical device 22 further includes a housing 38 that has a plurality of internal passageways and volumes, and from which vial spike 32 extends. Vial spike 32 includes two passageways: a longitudinally extending inlet passageway 40 that terminates at one end with an inlet opening 42, and a longitudinally extending outlet passageway 44 that terminates at one end with an outlet opening 46. As shown in FIG. 5B, outlet opening 46 is positioned higher along vial spike 32 or closer to the tip of the vial spike than inlet opening 42. Inlet opening 42 and inlet passageway 40 are in fluid communication with an internal, open-ended passageway 47 (FIG. 4A) of transfer spike 31 through a transfer channel 48 defined within housing 38 and a conduit 50 (e.g., a polymer tube) joining the transfer spike to the transfer channel. Thus, when medical device 22 is connected to reservoir 24 and vial 26, fluid 25 can flow from the reservoir, through passageway 47 in transfer spike 31, through conduit 50, through transfer channel 48, through inlet passageway 40, out inlet opening 42, and into the vial. As shown, medical device 22 includes a flow controller 52 (e.g., a tube clamp) associated with conduit 50 to control the flow of fluid 25 through the conduit.

Outlet opening 46 and outlet passageway 44 are capable of being in fluid communication with activation port 34 and outlet port 36. More specifically, medical device 22 includes a chamber 54 capable of being in fluid communication with outlet passageway 46, an activation channel 56 in fluid communication with the chamber, and an outlet channel 58 in fluid communication with the chamber. Activation channel 56 is in fluid communication with activation port 34 and is capable of being in fluid communication with syringe 28 when the syringe is engaged with the activation port. Outlet channel 58 is in fluid communication with outlet port 36 and is capable of being in fluid communication with target container 30 when the target container is engaged with the outlet port.

Referring to FIGS. 6A, 6B and 6C, the construction of chamber 54 and its associated features act as a one-way flow valve that allows fluid to flow substantially only one way through the chamber. Chamber 54 is defined by one or more walls 62 (e.g., for cylindrical or non-cylindrical chambers), a base 64, and a downwardly extending neck 66 (as viewed in FIG. 6A) that is coaxial with outlet channel 58. Wall(s) 62 and base 64 include channels or grooves 60 that extend longitudinally along the wall(s) and the chamber to be in fluid communication with outlet channel 58. Within chamber 54, medical device 22 includes a movable member 68 (e.g., a disc made of a polymer such as silicone or rubber) capable of translating between neck 66 and base 64, depending on the fluid pressure applied to the movable member. When there is no applied pressure, movable member 68 is at rest on base 64. When fluid flows from outlet passageway 44 and into chamber 54, pressure from the fluid flow lowers member 68 (as viewed in FIG. 6B) and forces the member to sit in contact against base 64. The fluid can continue to flow toward activation channel 56 (and syringe 28) and outlet channel 58 (and target container 30) by flowing in grooves 60 in wall(s) 62 and base 64 which are not obstructed by movable member 68. However, when fluid flows from activation channel 56 (e.g., when the plunger of syringe 28 is pushed) or outlet channel 58 into chamber 54, pressure from the fluid flow raises member 68 (as viewed in FIG. 6B) and forces the member to sit in contact against neck 66. As a result, inlet passageway 40 is sealed from chamber 54 and the fluid is prevented from flowing from the chamber into the inlet passageway.

Referring again to FIG. 4B, chamber 54 is also in fluid communication with an air vent 70 that allows air to be released from medical device 22 during transferring and mixing of liquid 25 and drug 27 while restricting air flow into the medical device, thereby acting as a one-way flow valve. As shown, within housing 38, chamber 54 is in fluid communication with a vent channel 72 that extends to be in fluid communication with a vent chamber 74. Within vent chamber 74, housing 38 has a first raised portion 76, a second raised portion 78, and a movable member 80 between portions 76, 78. First raised portion 76 (as shown, an annular portion protruding upwardly) extends around a vent inlet opening 82 that is between vent channel 72 and vent chamber 74. Second raised portion 78 (as shown, an annular portion protruding downwardly) extends around a vent outlet opening 84 that is between vent chamber 74 and the exterior environment. In some embodiments, medical device 22 includes a filter (e.g., a particulate filter and/or an anti-microbial filter) that extends over vent outlet opening 84 and is secured by second raised portion 78. The filter can prevent one or more selected materials from passing through vent outlet opening 84, for example, to contaminate drug 27, to expose personnel to an unwanted material, and/or to release a material into the exterior environment. The filter is prevented from contacting drug 27 and fluid 25 by movable member 80, which is responsive to the level of fluid (e.g., liquid) in vent chamber 74.

Indeed, movable member 80 is capable of moving between first and second raised portions 76, 78, depending on the level of fluid (e.g., liquid) in vent chamber 74, to seal vent inlet opening 82 or vent outlet opening 84. In some embodiments, movable member 80 includes (e.g., is formed entirely of) a buoyant material (e.g., having a specific gravity of one or less), such as a thin polymer (e.g., poly-isoprene). Materials having a specific gravity greater than one (e.g., polymers such as rubber, or silicone) can also be used, for example, by structurally and/or compositionally modifying the materials to produce the desired buoyancy. As examples, structural features, such as frames or circumferential rims, made of a more buoyant material can be incorporated, and air can be blown into the materials to form trapped air bubbles or a porous structure. As a result, when a liquid enters vent chamber 74 through vent channel 72 and vent inlet opening 82, movable member 80 moves along with the level of the liquid in the vent chamber and can be forced up (as viewed in FIG. 4B) to engage with second raised portion 78, thereby sealing vent outlet opening 84 and preventing fluid flow through the vent outlet opening. When there is no liquid in vent chamber 74, movable member 80 is at rest and engaged with first raised portion 76, thereby sealing vent inlet opening 82 and preventing fluid flow through vent inlet opening 82 and into vent channel 72.

Referring again to FIG. 1, in some embodiments, one-way flow device, such as a check valve or an anti-siphon valve, is placed to restrict fluid flow from target container 30 to medical device 22. For example, a check valve can be placed along outlet channel 58 and upstream of target container 30 to allow fluid to flow from medical device 22 to the target container, while restricting backflow of fluid. The one-way flow device can be selected to allow fluid to flow into target container 30 only at a selected pressure (e.g., a break through pressure) or greater (e.g., greater than approximately one atmosphere).

In operation, to combine liquid 25 with a drug 27, medical device 22 is placed in fluid communication with the other components of medical device system 20. More specifically, syringe 28 is connected to activation port 34, and target container 30 is connected to outlet port 36. Transfer spike 31 is engaged with reservoir 24 to place passageway 47, conduit 50 and transfer channel 48 in fluid communication with fluid 25. Vial spike 32 is engaged with vial 26 to place inlet and outlet passageways 40, 44 in fluid communication with drug 27.

Reservoir 24 is then elevated over inlet opening 42 of vial spike 32 (FIG. 1), thereby causing fluid 25 to flow from the reservoir into vial 26 and housing 38 and to combine with drug 27. Specifically, fluid 25 flows from reservoir 24, through passageway 47, through conduit 50, through transfer channel 48, out inlet opening 42, and into vial 26, thereby forming a combination of liquid 25 and drug 27 in the vial. Air in vial 26 and various volumes in housing 38 is displaced by fluid 25 flowing into medical device 22 and is allowed to exit the medical device through outlet passageway 44, chamber 54, vent channel 72 and air vent 70. The air that is displaced and purged can be equal to the volume created by the height of outlet opening 46 relative to the opening of vial 26. If fluid 25 enters outlet opening 46, the fluid can displace more air in medical device 22.

In some embodiments, the combination of fluid 25 and drug 27 in vial 26 flows into vent chamber 74 (via outlet passageway 44, chamber 54, and vent channel 72). The combination of fluid 25 and drug 27, upon entering vent chamber 74, can lift movable member 80 against second raised portion 78 to seal vent outlet opening 84 and air vent 70. As a result, exposure of the combination of drug 27 and fluid 25 to air is restricted. In some embodiments, the combination of fluid 25 and drug 27 is prevented from flowing into target container 30 by a flow device, as described above.

Syringe 28 is then used to provide a pumping action to further combine (e.g., mix) fluid 25 and drug 27 and to transfer of the combination into target container 30. First, the plunger of syringe 28 is withdrawn to create a negative pressure within housing 38 that draws the combination of fluid 25 and drug 27 from vial 26, through outlet passageway 44, through chamber 54, through activation channel 56, and into the syringe. The negative pressure and the transfer of fluid 25 and drug 27 from vial 26 result in more fluid from reservoir 24 being transferred into vial 26 via conduit 50, transfer channel 48, and inlet passageway 40. Also, depending on how forcefully or rapidly the plunger of syringe 28 is withdrawn, fluid 25 and drug 27 in vent chamber 74 (if any) can also be drawn into the syringe. If the plunger is withdrawn relatively slowly, the level of fluid 25 in vent chamber 74 can remain undisturbed, even as more fluid 25 is transferred from reservoir 24 into housing 38 and syringe 28. As a result, movable member 80 can remain engaged with second raised portion 78, and no air can enter vent chamber 74. If the plunger is withdrawn relatively quickly or forcefully, the level of fluid 25 in vent chamber 74 can fall, along with movable member 80, and air (e.g., filtered air) can enter into the vent chamber. No air, however, is drawn into medical device 22 beyond inlet vent opening 82 since this opening is sealed by movable member 80 contacting against first raised portion 76, or any remaining fluid 25 in vent chamber 74. In both cases, air is restricted from contaminating fluid 25 and drug 27, and being introduced into target container 30.

Next, the plunger of syringe 28 is pushed forward to transfer the combination of fluid 25 and drug 27 into target container 30. As the plunger is pushed, fluid 25 and drug 27 flow from syringe 28, through activation channel 56, through outlet channel 58, through the flow device (if any) and into target container 30. Fluid 25 and drug 27 can also flow into through activation channel 56 and into chamber 54, but the fluid and the drug are prevented from flowing back through outlet passageway 44 and into vial 26. As fluid 25 and drug 27 are pushed up into chamber 54 (as viewed in FIG. 6B), the fluid pressure forces movable member 68 against neck 66 and prevent fluid flow into outlet passageway 44. Furthermore, depending on how forcefully or rapidly the plunger of syringe 28 is pushed, fluid 25 and drug 27 can also flow from syringe 28, into chamber 54, through vent channel 72, and into vent chamber 74. In vent chamber 74, fluid 25 and drug 27 force (e.g., raise) movable member 80 against second raised portion 78, thereby sealing vent outlet opening 84. Again, air is restricted from entering into medical device system 20 and contaminating fluid 25 and drug 27, and release of the fluid and the drug from housing 38 is prevented. Any filter extending across outlet opening 84 is prevented from contacting fluid 25 and drug 27.

By repeating the above-described pumping action, fluid 25 in reservoir 24 can be transferred (partially or wholly) into vial 26, combined with drug 27, and subsequently transferred into target container 30. At any stage during transfer and combination, regardless of the position of the plunger of syringe 28, the user can shake medical device 22 to enhance mixing of fluid 25 and drug 27 in vial 26, housing 38, and/or the syringe.

In some embodiments, during use, flow controller 52 is used to control (e.g., to stop) the flow of fluid through conduit 50. For example, when only a portion of fluid 25 in reservoir 24 is to be combined with drug 27, flow controller 52 can limit the amount of fluid transferred through conduit 50. As another example, when multiple fluids 25 are to be combined with drug 27, flow controller 52 can temporarily shut off conduit 50 to allow transfer spike 31 to engage with other reservoirs 24 containing more fluid or different fluids, e.g., that is to be transferred in a selected sequence.

In some embodiments, after the combination of drug 27 and fluid 25 are in target container 30, the amount of any air in vial 26 is less than the amount of air in the vial prior to combination and transfer of the materials, i.e., there can be a slight negative pressure within medical device system 20, which indicates that air cannot enter the medical device system. The transferred combination of drug 27 and fluid 25 can be administered from target container 30 to a patient, for example.

While a number of embodiments have been described, the invention is not so limited.

For example, in some embodiments, vial spike 32 is not unitarily formed with housing 38 as shown above, but the vial spike is in fluid communication with housing 38 through one or more conduits.

Other piercing members besides spikes can be used. For example, a piercing member can be a needle or a sharp-tipped tubing having one or more passageways.

Other pumps besides syringe 28, such as a squeeze bulb, can be used. The pumps can be mechanically-driven and/or electrically-driven.

In some embodiments, alternatively or additionally to having chamber 54, medical device 22 includes a one-way flow valve between outlet passageway 44 and activation channel 56 and outlet channel 58. The one-way flow valve can be arranged to allow fluid (e.g. liquid) to flow from outlet passageway 44 and into activation channel 56 and outlet channel 58, while restricting backflow of fluid into the outlet passageway.

In some embodiments, alternatively or additionally to having air vent 70, medical device 22 includes a one-way flow valve in fluid communication with vent channel 72. The one-way flow valve can be placed anywhere between chamber 54 and an opening that is in fluid communication with the exterior environment, such as vent outlet opening 84. For example, the one-way flow valve can be placed along vent channel 72, at vent inlet opening 82, and/or at vent outlet opening 84. The one-way flow valve allows fluid (e.g., air) to flow from chamber 54 into the exterior environment (e.g., to vent medical device 22 during fluid transfer) while restricting backflow of fluid into the chamber.

Movable member 80 can have any of a variety of shapes. For example, movable member 80 can be a circular disc having circumferential rims that facilitate seating and sealing against first and second raised portions 76, 78. Movable member 80 can be an appropriately sized sphere that can engage with first and second raised portions 76, 78 and seal vent inlet opening 82 and vent outlet opening 84. In some embodiments, medical device 22 includes a structure that can guide the movement of the sphere, such as a cylinder having a perforated wall and extending between vent inlet opening 82 and vent outlet opening 84, and in which the sphere can move.

In some embodiments, medical device 22 includes multiple transfer spikes 31 and transfer channels 48 in fluid communication with inlet passageway 40 to allow multiple fluids to be combined with drug 27.

Drug 27 can be in liquid form, solid form (e.g. powder), or a combination of one or more liquids and one or more solids (e.g., a colloidal suspension). More than one drug 27 and/or more than one liquid 25 can be transferred and combined using the embodiments described herein.

Terms, such as "up", "down", "downwardly", and "upwardly", are used to describe the embodiment as shown in the orientation of the figures, and not intended to be limiting.

Still other embodiments are within the scope of the following claims.

What is claimed is:

1. A medical device system, comprising:

a medical device comprising a housing configured to be placed in fluid communication with a first container containing a drug, a second container containing a liquid, a pump, and a third container, the housing defining a fluid chamber and a vent chamber in fluid communication with the fluid chamber, wherein the medical device is configured to combine the liquid and the drug in the first container, to transfer the liquid and the drug from the first container to the fluid chamber and the vent chamber, and to transfer the liquid and the drug from the fluid chamber and the vent chamber to the third container;

wherein negative pressure within the housing draws the liquid and the drug from the first container and the vent chamber through the fluid chamber; and wherein positive pressure within the housing forces the liquid and the drug into the third container.

2. The system of claim 1, wherein the medical device comprises a one-way flow valve adapted to restrict flow of the liquid from the housing to the first container.

3. The system of claim 1, wherein the medical device comprises a valve adapted to restrict air flow into the housing.

4. The system of claim 1, wherein the medical device comprises a valve adapted to restrict air flow into the housing and to allow air flow out of the housing.

5. The system of claim 4, wherein the valve comprises a movable member responsive to a level of liquid in a chamber containing the movable member.

6. The system of claim 1, wherein the medical device comprises a valve adapted to restrict liquid flow into the third container.

7. The system of claim 1, wherein the medical device comprises a one-way flow valve adapted to restrict liquid flow from the third container to the housing.

8. The system of claim 1, wherein the medical device comprises at least two one-way flow valves in the housing.

9. The system of claim 1, wherein the medical device comprises at least three flow valves in the housing.

10. The system of claim 1, wherein the medical device comprises at least two piercing elements in fluid communication with the housing.

11. The system of claim 1, wherein the medical device comprises an air filter, and the medical device is configured to restrict the air filter from contacting the liquid.

12. The system of claim 1, further comprising the first container, the second container, the pump in the form of a syringe, and a third container.

13. The system of claim 1, further comprising a conduit integrally connected to the housing, the conduit facilitating the fluid communication between the housing and the second container and allowing the second container to be positioned remotely from the medical device.

* * * * *